US012683030B2

(12) United States Patent
Sanchez et al.

(10) Patent No.: US 12,683,030 B2
(45) Date of Patent: Jul. 14, 2026

(54) PROXY MODEL USING MOBILE DEVICE DATA TO PROVIDE HEALTH INDICATORS

(71) Applicant: Quanata, LLC, San Francisco, CA (US)

(72) Inventors: Kenneth J. Sanchez, San Francisco, CA (US); Bennett Smith, Inver Grove Heights, MN (US)

(73) Assignee: QUANATA, LLC, San Francisco, CA (US)

( * ) Notice: Subject to any disclaimer, the term of this patent is extended or adjusted under 35 U.S.C. 154(b) by 0 days.

(21) Appl. No.: 18/732,348

(22) Filed: Jun. 3, 2024

(65) Prior Publication Data

US 2024/0321463 A1 Sep. 26, 2024

Related U.S. Application Data

(63) Continuation of application No. 15/880,043, filed on Jan. 25, 2018, now Pat. No. 12,002,587.

(51) Int. Cl.
| | |
|---|---|
| *G16H 50/30* | (2018.01) |
| *G06N 3/08* | (2023.01) |
| *G16H 50/50* | (2018.01) |

(52) U.S. Cl.
CPC ............... *G16H 50/30* (2018.01); *G06N 3/08* (2013.01); *G16H 50/50* (2018.01)

(58) Field of Classification Search
CPC ........... G16H 50/30; G16H 50/50; G06N 3/08
USPC ............................................................ 705/2
See application file for complete search history.

(56) References Cited

U.S. PATENT DOCUMENTS

| | | | |
|---|---|---|---|
| 2006/0228681 A1 | 10/2006 | Clarke | |
| 2014/0247155 A1* | 9/2014 | Proud .................... | A61B 5/681 |
| | | | 340/870.01 |
| 2017/0316313 A1* | 11/2017 | Corrado ................. | G06N 3/09 |
| 2019/0172579 A1* | 6/2019 | Peterson ............... | G16H 40/67 |

FOREIGN PATENT DOCUMENTS

| | | |
|---|---|---|
| WO | 2011088044 | 7/2011 |
| WO | 2017147552 | 8/2017 |

OTHER PUBLICATIONS

Kakria, P., Tripathi, N. K., & Kitipawang, P. (2015). A real-time health monitoring system for remote cardiac patients using smartphone and wearable sensors. International journal of telemedicine and applications, 2015(1), 373474. (Year: 2015).*

(Continued)

*Primary Examiner* — Winston R Furtado
(74) *Attorney, Agent, or Firm* — BRYAN CAVE LEIGHTON PAISNER LLP

(57) ABSTRACT

A computer-implemented method for health assessment includes providing an artificial neural network trained with training data. The method also includes receiving activity data comprising personal activity metrics corresponding to a target person, and determining, by the artificial neural network, a health indicator of the target person based upon the activity data corresponding to the target person. The method further includes outputting the health indicator of the target person to an electronic device for communication of the health indicator to a user of the electronic device. Other embodiments are disclosed.

20 Claims, 4 Drawing Sheets

(56) References Cited

OTHER PUBLICATIONS

Studenski, S., Perera, S., Patel, K., Rosano, C., Faulkner, K., Inzitari, M., . . . & Guralnik, J. (2011). Gait speed and survival in older adults. Jama, 305(1), 50-58. (Year: 2011).*

Carroll, J. K., Moorehead, A., Bond, R., LeBlanc, W.G., Petrella, R. J., & Fiscella, k. (2017). Who uses Mobile Phone Health Apps and Does Use Matter? A Secondary Data Analytics Approach. Journal of medical Internet research, 19(4), e125. doi:10.2196/jmir.5604 2017.

* cited by examiner

200

300

TRAIN, USING LABELED TRAINING DATA
PROXY MODEL TO ENABLE THE PROXY MODEL
TO DETERMINE HEALTH INDICATORS OF
PERSONS BASED UPON PERSONAL ACTIVITY    302

RECEIVE AN ACTIVITY DATA SET
CORRESPONDING TO TARGET PERSON    304

DETERMINE A HEALTH INDICATOR OF THE
TARGET PERSON, AT LEAST BY
PROCESSING THE ACTIVITY DATA SET
USING THE TRAINED PROXY MODEL    306

PROXY MODEL USING MOBILE DEVICE DATA TO PROVIDE HEALTH INDICATORS

CROSS-REFERENCE TO RELATED APPLICATIONS

This application is a continuation of U.S. patent application Ser. No. 15/880,043, filed Jan. 25, 2018. U.S. patent application Ser. No. 15/880,043 is incorporated herein by reference in its entirety.

FIELD OF THE DISCLOSURE

The present disclosure generally relates to human health assessments and, more particularly, to computer-implemented models for assessing human health.

BACKGROUND

Conventional methods for assessing health of a person may be invasive and require active, time-consuming participation on the part of the person. For example, the person may be required to undergo invasive, time-consuming, and/or costly physical testing, to provide family medical history documentation, etc. Unfortunately, this active participation may be a prerequisite for offering health or life related products (e.g., insurance products) to the person. Moreover, the reliability of conventional health assessment methods may rely on the person's ability and willingness to fully and accurately report information that may be relevant to the person's short and long term health. Further, conventional heath assessments can impose substantial costs on the entity performing or requesting the assessment. For example, analyzing a person's medical records and/or exam results can require a significant amount of time.

SUMMARY

Generally, the present disclosure describes systems and methods for determining health indicators (e.g., life expectancies) of "target persons" using a proxy model comprising an artificial neural network, in lieu of traditional and/or more complex/costly/intrusive health assessment processes (e.g., conventional underwriting processes). Prior to using the artificial neural network to determine the health indicators of target persons, the artificial neural network may be constructed using labeled training data corresponding to a number of "training persons." The labeled training data may comprise a plurality of activity data training sets, with each set including personal activity metrics associated with activities performed by a respective training person, and with at least some of the metrics of a given set being obtained or derived from one or more mobile electronic devices (e.g., a smartphone and/or a wearable device) of the respective training person. Once trained, the artificial neural network may process activity data sets associated with the target persons to determine respective health indicators.

In one embodiment, a computer-implemented method for health assessment can comprise providing an artificial neural network trained with training data, wherein the training data comprises training metrics and health indicators corresponding to training persons, wherein the training data is based on data from mobile electronic devices associated with the training persons, and wherein the artificial neural network is trained by at least identifying one or more first ones of the training metrics as having one or more predicted effects on one or more of the health indicators; receiving activity data comprising personal activity metrics corresponding to a target person, wherein the activity data is based on data from one or more sensors associated with the target person and associated with one or more of the training metrics; determining, by the artificial neural network, a health indicator of the target person based upon the activity data corresponding to the target person; and outputting the health indicator of the target person to an electronic device for communication of the health indicator to a user of the electronic device.

In one embodiment, a computer-implemented method for determining a health indicator of a target person may be provided, the method using a proxy model as a proxy for a health assessment process, and the method comprising (1) training, by one or more processors and using labeled training data, the proxy model to enable the proxy model to determine health indicators of persons based upon personal activity, wherein the proxy model is an artificial neural network, wherein the labeled training data includes a plurality of activity data training sets each corresponding to a different one of a plurality of training persons, and wherein each of the activity data training sets (i) includes a suite of personal activity metrics obtained or derived from one or more mobile electronic devices of the respective training person, and (ii) is labeled by a health indicator assigned to the respective training person by the health assessment process, (2) receiving, by the one or more processors, an activity data set corresponding to the target person, wherein the activity data set includes a suite of personal activity metrics obtained or derived from one or more mobile electronic devices of the target person, and (3) determining, by the one or more processors, a health indicator of the target person, at least by processing the activity data set using the trained proxy model. The method may comprise additional, alternate, or fewer elements, including those described herein.

In another embodiment, a computer system for health assessment can comprise one or more processors; and one or more memories storing computer-executable instructions that, when executed by the one or more processors, cause the computing system to provide an artificial neural network trained with training data, wherein the training data comprises training metrics and health indicators corresponding to training persons, wherein the training data is based on data from mobile electronic devices associated with the training persons, and wherein the artificial neural network is trained by at least identifying one or more first ones of the training metrics as having one or more predicted effects on one or more of the health indicators; receive activity data comprising personal activity metrics corresponding to a target person, wherein the activity data is based on data from one or more sensors associated with the target person and associated with one or more of the training metrics; determine, by the artificial neural network, a health indicator of the target person based upon the activity data corresponding to the target person; and output the health indicator of the target person to an electronic device for communication of the health indicator to a user of the electronic device.

In another embodiment, a computing system configured to determine a health indicator of a target person may be provided, the computing system using a proxy model as a proxy for a health assessment process, and the computing system comprising (1) one or more processors, and (2) one or more memories storing computer-executable instructions that, when executed via the one or more processors, cause the computing system to (i) train, by the one or more processors and using labeled training data, the proxy model to enable the proxy model to determine health indicators of persons based upon personal activity, wherein the proxy model is an artificial neural network, wherein the labeled training data includes a plurality of activity data training sets each corresponding to a different one of a plurality of training persons, and wherein each of the activity data training sets (i) includes a suite of personal activity metrics obtained or derived from one or more mobile electronic devices of the respective training person, and (ii) is labeled by a health indicator assigned to the respective training person by the health assessment process; (ii) receive, by the one or more processors, an activity data set corresponding to the target person, wherein the activity data set includes a suite of personal activity metrics obtained or derived from one or more mobile electronic devices of the target person; and (iii) determine, by the one or more processors, a health indicator of the target person, at least by processing the activity data set using the trained proxy model. The computing system may include additional, fewer, or alternate components or functions thereof, including those described herein.

In yet another embodiment, a non-transitory, computer-readable medium for health assessment can store instructions that, when executed by one or more processors, cause the one or more processors to provide an artificial neural network trained with training data, wherein the training data comprises training metrics and health indicators corresponding to training persons, wherein the training data is based on data from mobile electronic devices associated with the training persons, and wherein the artificial neural network is trained by at least identifying one or more first ones of the training metrics as having one or more predicted effects on one or more of the health indicators; receive activity data comprising personal activity metrics corresponding to a target person, wherein the activity data is based on data from one or more sensors associated with the target person and associated with one or more of the training metrics; determine a health indicator of the target person based upon the activity data corresponding to the target person; and output the health indicator of the target person to an electronic device for communication of the health indicator to a user of the electronic device.

In yet another embodiment, a non-transitory, computer-readable medium for determining a health indicator of a target person using a proxy model as a proxy for a health assessment process may be provided. The computer-readable medium may store instructions that, when executed by one or more processors, cause the one or more processors to: (1) train, using labeled training data, the proxy model to enable the proxy model to determine health indicators of persons based upon personal activity, wherein the proxy model is an artificial neural network, wherein the labeled training data includes a plurality of activity data training sets each corresponding to a different one of a plurality of training persons, and wherein each of the activity data training sets (i) includes a suite of personal activity metrics obtained or derived from one or more mobile electronic devices of the respective training person, and (ii) is labeled by a health indicator assigned to the respective training person by the health assessment process; (2) receive an activity data set corresponding to the target person, wherein the activity data set includes a suite of personal activity metrics obtained or derived from one or more mobile electronic devices of the target person; and (3) determine, by the one or more processors, a health indicator of the target person, at least by processing the activity data set using the trained proxy model. The computer-readable medium may include additional, fewer, or alternate instructions, including those described herein.

BRIEF DESCRIPTION OF THE DRAWINGS

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

DETAILED DESCRIPTION

Figure 1:
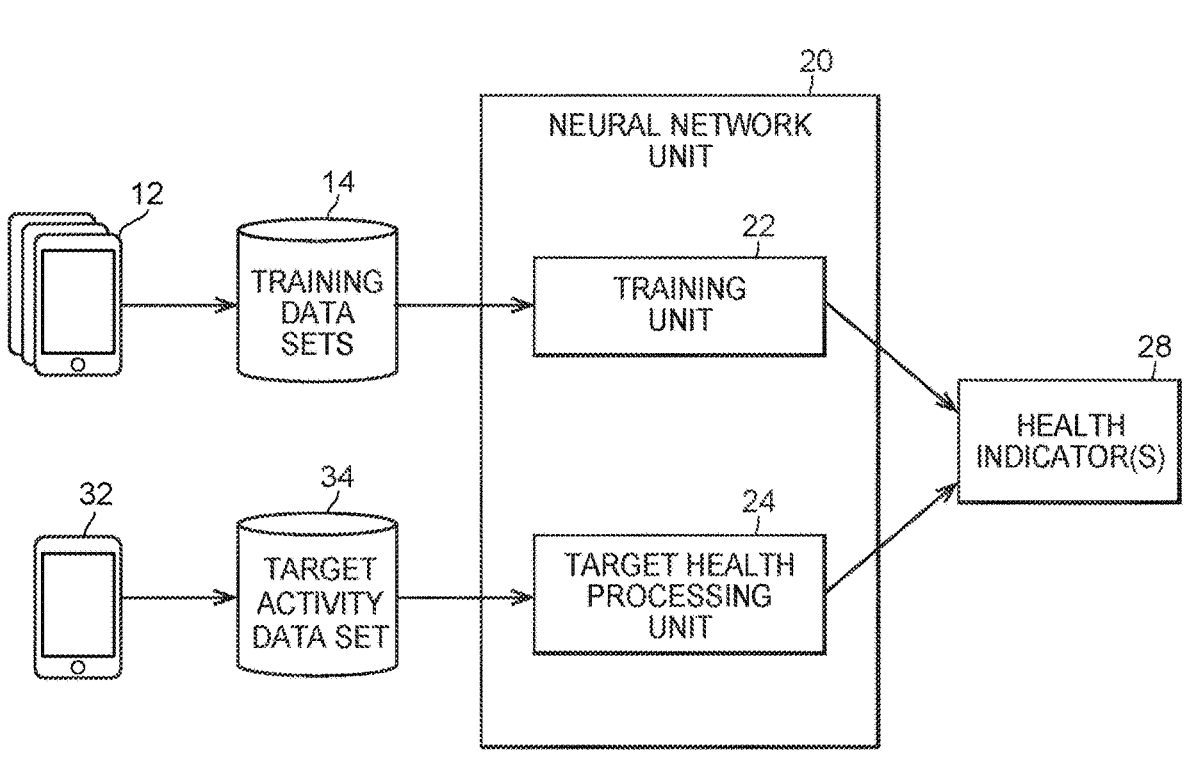
FIG. 1 is a data flow diagram showing an example technique for determining health indicators of respective persons, in accordance with some embodiments.

The present embodiments may relate to, inter alia, systems and methods for determining a health indicator of a person, such as the person's life expectancy, life or health insurance premium, or overall "health score," using a model (e.g., an artificial neural network) as a proxy for a traditional, complex, costly, and/or intrusive health assessment process. While this latter type of health assessment process may be time consuming, costly, and/or invasive for the person being assessed, the proxy model may be trained to determine a health indicator based upon personal activity metrics that are much more easily, efficiently, and/or accurately obtained (e.g., metrics derived from sensor data via from the smartphone, smart wearable device, and/or other mobile electronic device(s) of the person being assessed).

Generally, the proxy model may be constructed from labeled training data associated with "training persons," wherein each training person is associated with a known health indicator (e.g., as determined using another health assessment process, such as a traditional life insurance underwriting process). The labeled training data may comprise an activity data training set associated with each respective training person, with each activity data training set including a plurality (or "suite") of personal activity metrics obtained (or derived from sensor data obtained) by a mobile electronic device associated with the training person. In other words, each activity data training set is associated with a known health indicator of the respective training person. Based upon this known or "labeled" relationship, the proxy model may be constructed (i.e., trained). The training may be complete when the proxy model outputs, for some or all of the activity data training sets, a health indicator that matches (exactly, or within some acceptable margin of error) the known health indicator of the respective training person.

Knowledge gained from the training of the proxy model may, in some embodiments, include identification of those particular personal activity metrics that are most strongly correlated with the health indicator of a person (i.e., activity metrics having a significant predictive effect on the health indicator). Based upon this knowledge, a party intending to acquire an activity data set from a target person may, for example, configure a mobile device application (e.g., an application downloaded to the mobile electronic device of the target person) to activate and/or access only those particular sensors that are needed to obtain sensor data associated with (i.e., usable to derive) the personal activity metrics that are most strongly predictive of the health indicator.

Once the proxy model is trained to accurately determine health indicators of the training persons (and possibly, for verification purposes, health indicators of "test" persons that are associated with labeled data but were not used to train the proxy model), the trained proxy model may be utilized for any number of "target persons" whose health indicators are unknown. In particular, for each such target person, the trained proxy model may receive as input an activity data set corresponding to the target person, and produce as output a health indicator of the target person.

Example Environment For Determining Health Indicators of Persons

FIG. 1 is a data flow diagram showing an example technique 10 for determining health indicators of respective persons, in accordance with some embodiments. In the example technique 10, one or more mobile electronic devices 12 (e.g., including smartphones, smart wearable devices, etc.) may be associated with one or more respective training persons (e.g., persons carrying and/or wearing one or more of respective devices 12). Each of the mobile electronic devices 12 may include one or more sensors, such as a positioning sensor (e.g., a GPS unit), an accelerometer, a gyroscope, a thermometer, a barometer, a light sensor, a microphone, a camera, and/or other sensors. "Sensors," as referred to herein, may further include computing elements configured specifically to perform processing on raw data acquired via the sensors (e.g., an Apple™ Core Motion unit).

Each of mobile electronic devices 12 may be configured to collect (e.g., continuously, at predetermined intervals of time, automatically or upon a request by a user or another entity, etc.) sensor data via one or more sensors. In some embodiments, each device 12 may include, installed in a memory, an application configured to collect and/or transmit sensor data for the purpose of training a neural network, as further described below.

Sensor data from a given one or more electronic devices 12 may be analyzed to identify (i.e., "derive") one or more personal activity metrics associated with the person having (e.g., carrying or wearing) the one or more devices 12. In some embodiments, the device 12 may analyze the sensor data to identify one or more personal activity metrics. In other embodiments, the mobile electronic device 12 may transmit "raw" sensor data to another computing entity (e.g., a remote server), which may be configured to identify one or more personal activity metrics based upon the received sensor data. It should be appreciated that a combination of the above techniques may be utilized.

In just one example, an accelerometer of a device 12 may obtain accelerometer data during a period of time, the accelerometer data potentially being indicative of motion of the device 12 (and hence, the motion of a person having or wearing the device 12). A positioning sensor unit may, during the same period of time, obtain positioning data that is potentially indicative of a location of the device 12 (and hence, a location of the person having/wearing the device 12) during the period of time. At the device 12 and/or at the other computing entity, the sensor data may be analyzed to identify one or more personal activity metrics associated with the person having/wearing the device 12. It may be determined, for example, that the person walked or ran during the period of time, or more particularly, that the person walked or ran at a particular location (e.g., a gym), or at a particular average speed, etc. Sensor data obtained at a multiplicity of times may be analyzed to identify higher level personal activity metrics, such as average running speed, average time spent running per week/month/etc., or a typical time of day during which the person most often exercises.

In any case, a suite of identified personal activity metrics associated with any one person may be referred to as an "activity data set" associated with the person. Accordingly, each of a plurality of training data sets 14 may include an activity data set (i.e., suites of personal activity metrics) derived from sensor data obtained via mobile electronic devices 12 of respective training persons. Each of the training data sets 14 may further include one or more "known" health indicators associated with the respective training person, as determined by a particular health assessment process (e.g., an underwriting process based upon medical history, physical examination, etc.). The known health indicators of the training persons may be received from the respective mobile electronic devices 12 of the respective training persons, and/or via other sources. In this sense, the training data sets 14 may be understood as being "labeled" with known health indicators associated with respective persons.

A neural network unit 20 may be software that is generally configured to predict health indicators for different suites of personal activity metrics. The neural network unit 20 may comprise a training unit 22 and a target health processing unit 24. The training unit 22 may be configured to receive the labeled training data sets 14 (i.e., at least some of the personal activity metrics included therein) as inputs to an artificial neural network. The neural network may be any suitable type of computer-implemented neural network, such as a recurrent neural network or a feed-forward neural network. The neural network may comprise a plurality of nodes, also referred to herein as "neurons," arranged in a plurality of layers, and each neuron may process one or more inputs to generate one or more outputs (e.g., a decision or another value). The training unit 22 may train the neural network to generate "correct" health indicator outputs 28 associated with activity data sets of the respective training persons, i.e., health indicators that match (within some acceptable margin of error) the known health indicators (within the labeled training data sets 14) that were supplied to the training unit 22. Example neural networks and the elements thereof will be discussed further herein, in particular with regard to FIGS. 3 and 4.

A mobile device 32 of a target person may be configured to obtain sensor data corresponding to the target person for whom a health indicator is unknown, but desired. Personal activity metrics associated with the target person may be derived (e.g., at the mobile device 32 and/or at another computing entity) from the obtained sensor data. While one mobile device 32 is depicted herein, it should be understood that two or more mobile devices 32 of a target person (e.g., a combination of a smartphone and a smart wearable device)

are possible. The mobile electronic device 32 may be a device similar to any of the devices 12, for example, and may operate similarly to obtain sensor data corresponding to the target person. Accordingly, a target activity data set 34 may include a suite of personal activity metrics derived from sensor data obtained via the device 32. Once the neural network has been trained, the target health processing unit 24 of the neural network unit 20 may receive, as one or more inputs, the one or more personal activity metrics included in the target activity data set 34.

Generally, the personal activity metrics included in the target activity data set 34 may include similar metrics to those included in the training data sets 14. However, because the significance (i.e., predictive significance of a health indicator) of any particular personal activity metric may be unknown in a training phase, some or all of training data sets 14 may include more types of personal activity metrics than are included in the target activity data set 34. In other words, training data sets 14 may include one or more personal activity metrics that, as may be determined later via training of the artificial neural network, are not significant in determining a health indicator of the target person. Accordingly, the target activity data set 34 may not include the one or more metrics that are not significant.

In some embodiments, the device 32 may be equipped with an application configured to obtain sensor data, identify personal activity metrics, and/or transmit the sensor data and/or metrics. Based upon the trained neural network's identification of metrics that are or are not relevant to accurately determining a health indicator, the application may be specifically configured to control or access one or more sensors of the device 32 to obtain targeted sensor data associated with metrics most predictive of a health indicator. Targeted sensor data may include, for example, data collected via a particular one or more particular sensors, data collected at a particular time, interval, or frequency (e.g., a predetermined "heartbeat" interval), and/or data collected when the device 32 is at a particular location. For instance, if the training unit 22 had assigned a very small weight to certain metrics during the training process (e.g., a weight below some threshold level), the application may not obtain and/or transmit any sensor data that constitutes (or is used to derive) those relatively insignificant metrics. Thus, the application may be configured in such a manner to reduce or eliminate unnecessary activation of sensors, thereby reducing or eliminating unnecessary battery usage of, and/or processing within, the device 32.

Figure 2:
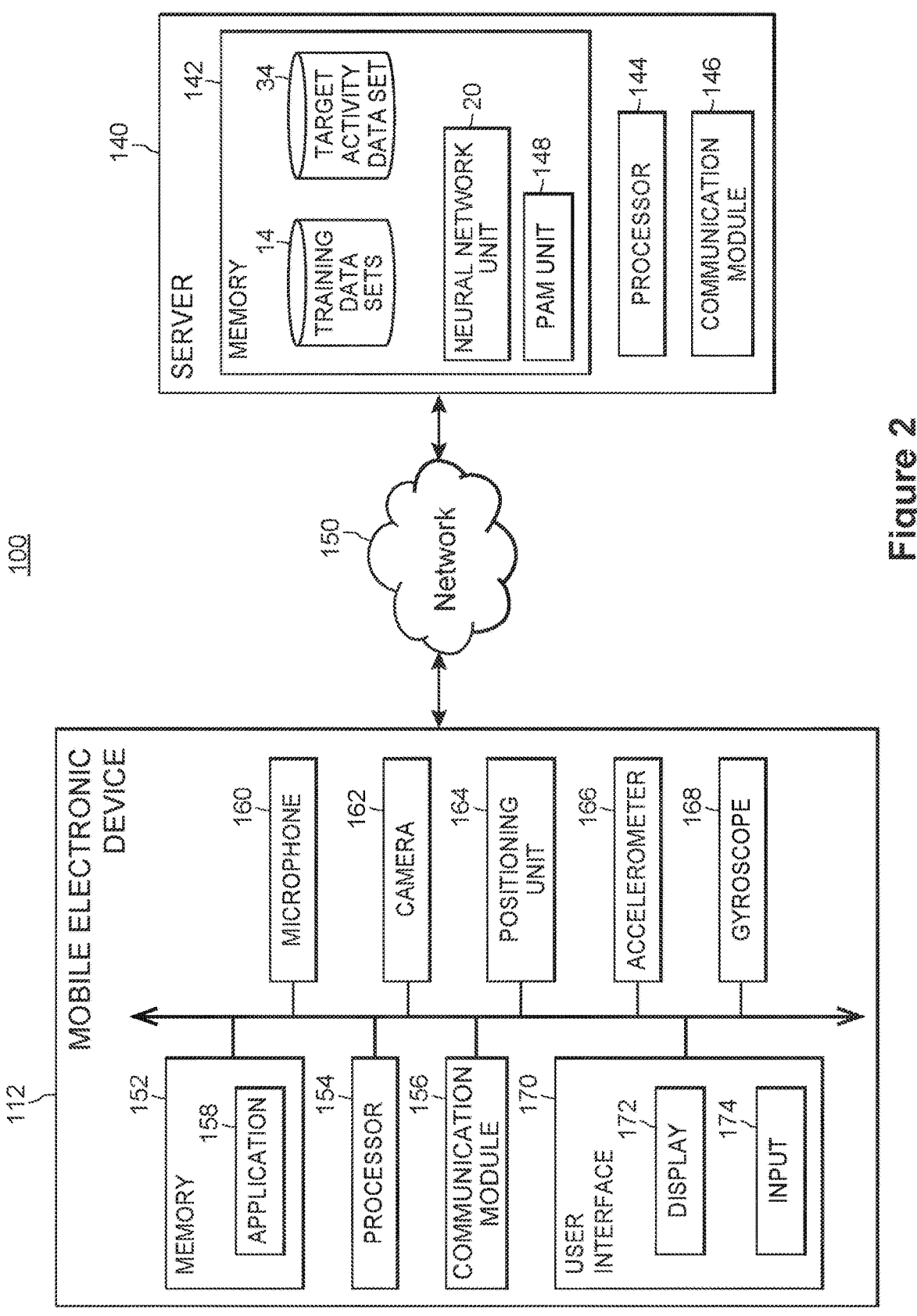
FIG. 2 is a block diagram showing an example environment in which the technique of FIG. 1 may be implemented, in accordance with some embodiments.

FIG. 2 depicts an environment 100 in which the technique 10 of FIG. 1 may be implemented, in accordance with some embodiments. The environment 100 generally includes a mobile electronic device 112 communicatively coupled to a server 140 via a network 150. The mobile electronic device 112 may correspond to one or more mobile electronic devices 12 (i.e., devices of one or more respective training persons) and/or one or more mobile electronic devices 32 (i.e., one or more devices of the target person) of FIG. 1. While one mobile electronic device 112 is illustrated in FIG. 2, it should be understood that a plurality of mobile electronic devices of respective training persons and/or target persons may be envisioned. In other words, in some embodiments, two or more mobile electronic devices 112 may be associated with a single training person or target person. Additional, fewer, or alternate components of the environment 100, and/or additional, fewer, or alternate actions thereof, may be envisioned, in some embodiments.

The mobile electronic device 112 and the server 140 may communicate via the network 150. The network 150 may include one or more wired and/or wireless local area networks (LANs), and/or one or more wired and/or wireless wide area networks (WANs) such as the Internet.

While the server 140 is referred to in the singular, the server 140 may include one or more distinct servers (e.g., distributed servers of a backend server farm). The server 140 includes a memory 142 (i.e., one or more memories). The memory 142 may include ROM, RAM, and/or other types of computer memory, and may include computer-executable instructions to be executed via a processor (i.e., one or more processors) 144. Generally, the computer-executable instructions, when executed via the processor 144, may cause the server 140 to receive or obtain, via a communication module 146, sensor data and/or personal activity metrics from the device 146, and/or derive personal activity metrics from received or obtained sensor data via a Personal Activity Metric (PAM) unit 148.

In some embodiments, the server 140 may receive personal activity metrics from the mobile electronic device 112 via the network 150. In other words, the mobile electronic device 112 may be configured to obtain sensor data, identify one or more personal activity metrics therefrom, and transmit the one or more identified personal activity metrics to the server 140. In some embodiments, though, the mobile electronic device 112 may obtain sensor data and transmit the sensor data to the server 140, and the server 140 may derive at least some personal activity metrics (e.g., via the PAM unit 148) based upon the received sensor data. It should be understood that a combination of the above described techniques may be employed.

In any case, the derived personal activity metrics may be stored at the memory 142. Suites of personal activity metrics corresponding to respective training persons may be stored as the training data sets 14, and a suite of personal activity metrics corresponding to the target person may be stored as the target activity data set 34.

The memory 142 may further include the neural network unit 20, which may be implemented as a software module, for example, and may be configured to (i) train the artificial neural network using the training data sets 14, and (ii) utilize the trained artificial neural network to determine a health indicator of the target person, based upon the target activity data set 34, as discussed above.

The mobile electronic device 112 may include a memory (i.e., one or more memories) 152. The memory 152 may include a ROM, RAM, and/or other computer memories. The memory 152 may include computer-executable instructions that, when executed via a processor (i.e., one or more processors) 154, cause the mobile electronic device 152 to obtain sensor data via one or more sensors at the mobile electronic device 112, derive personal activity metrics from the obtained sensor data, and/or communicate with the server 140 over the network 150, via the processor 154 and/or a communication module 156.

The computer-executable instructions may, in some embodiments, be included within an application 158 configured specifically to activate and/or access sensors to obtain sensor data associated with a training person or the target person (i.e., the person having the mobile electronic device 112). Sensors obtaining sensor data may include a microphone 160, a camera (and/or another imaging unit) 162, a positioning unit (e.g., GPS) 164, an accelerometer 166, a gyroscope 168, and/or other sensors, including those described herein. In some embodiments, the application 158 may further process obtained sensor data to identify activities performed by (i.e., personal activity metrics associated with) a user of the device 112. The mobile electronic device 112 may transmit the obtained sensor data and/or the identified personal activity metrics to the server 140 via the network 150. The mobile electronic device 112 may transmit acquired and/or derived personal activity metrics via the processor 154, and/or communication module 156, to the server 140 over the network 150.

In some embodiments, the mobile electronic device 112 may include one or more user interfaces 170, which may include one or more displays 172 and/or one or more input devices 174 (e.g., a touch screen, keypad, etc.) via which a user of the device 112 may interact with the device 112. In some embodiments, the user may utilize the user interface(s) 170 to expressly "opt-in" to the sensor data collection functionalities described herein (e.g., via the application 158). An "opt-in" may include a user acceptance of collection of sensor data (via one or more particular sensors) for purposes of neural network training and/or health indicator determination, as described herein.

In some embodiments, the neural network unit 20, or at least some functions or components thereof, may be disposed at the mobile electronic device 112. For example, the neural network unit 20 (or more specifically, the target health processing unit 24 depicted in FIG. 1) may be disposed at a mobile electronic device 112 of the target person. In these embodiments, the mobile electronic device 112 may cause training of the artificial neural network, and/or cause the artificial neural network to be utilized to determine the health indicator of the target person.

Additional, fewer, and/or alternate components of the environment 100 may be possible, in some embodiments.

Example Elements of an Artificial Neural Network

Figure 3:
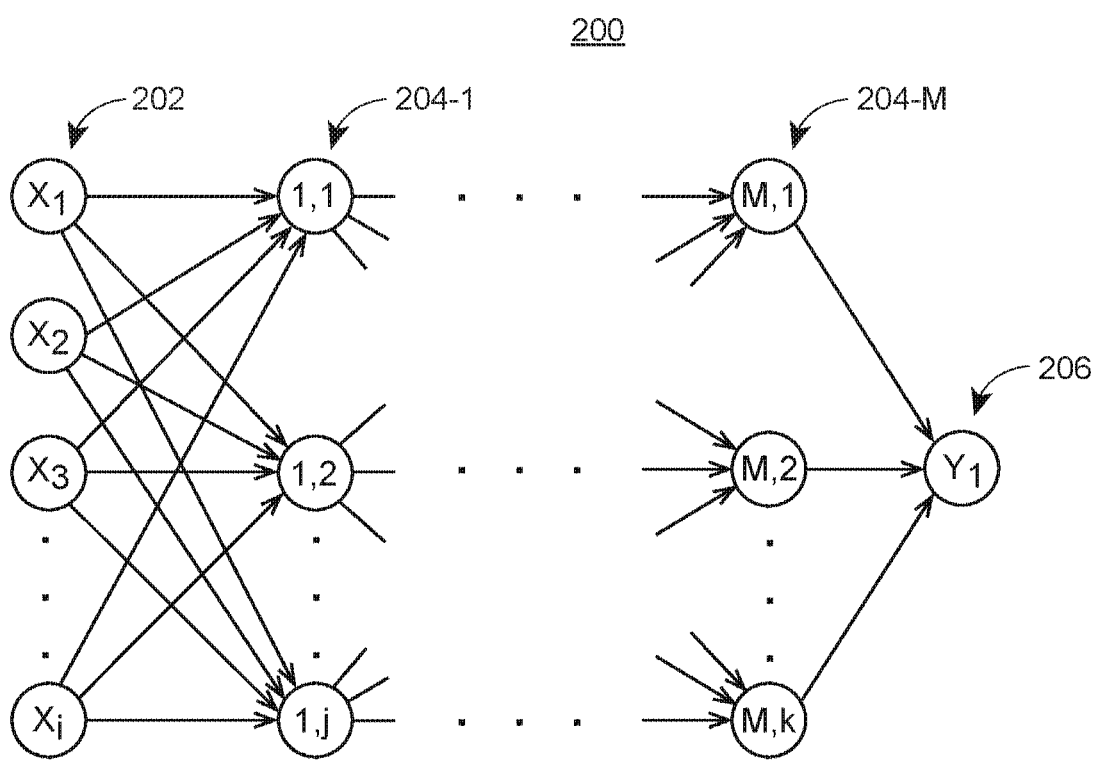
FIG. 3 depicts an example artificial neural network that may be trained to determine health indicators of persons, in accordance with some embodiments.

FIG. 3 depicts an example artificial neural network 200 that may be trained to determine health indicators of persons based upon activity data sets obtained or derived from mobile electronic devices, according to some embodiments. The neural network 200 may be trained, for example, by the neural network unit 20 (or more specifically, the training unit 22) of FIG. 1 and/or the neural network unit 120 of FIG. 2. The neural network 200, once trained, may be utilized via the same neural network unit 20 (specifically, the target health processing unit 24) of FIG. 1 and/or neural network unit 120 of FIG. 2.

The neural network 200 includes a multiplicity of neurons arranged in multiple layers, and includes an input layer 202, a number of intermediate (also referred to herein as "hidden") layers 204-1 through 204-M, and an output layer 206. M may be any integer greater than or equal to one. Each of the layers 202, 204-1 through 204-M, and 206 may have any number of inputs/neurons/outputs (e.g., the layer 204-1 including neurons "1, 1" through "1, j," wherein j represents the number of neurons in layer 204-1). Other configurations of the neural network 200 are possible.

The input layer 202 may correspond to personal activity metrics that may be obtained or derived from mobile electronic devices (e.g., a device 12, 32, and/or 112). Accordingly, each input $x_1$ through $x_i$(wherein i represents the number of inputs) of the input layer 202 may correspond to a particular personal activity metric, such as a measure of a particular activity performed by a person having a mobile electronic device (e.g., average or total hours spent walking per week, average walking speed, average or total hours slept per night, etc.). The input layer 202 may have any number i of inputs. In some embodiments, the number of inputs used by the neural network 200 during training may be greater than the number of inputs used by the neural network after training.

Each of the intermediate layers 204-1 through 204-M may include any number of neurons, and a different number of neurons at each layer is possible. Each intermediate layer neuron may operate on one or more inputs from the input layer 202 and/or one or more outputs of other layers (e.g., the preceding intermediate layer), to generate a decision or other output.

The output layer 206 may include one or more outputs (only one output $y_1$ is shown), each corresponding to a health indicator (e.g., a life expectancy, a life insurance premium, a health score, etc.) associated with a person. In some embodiments, outputs of the neural network 200 may be obtained not just from the output layer 206, but also from one or more of the intermediate layers 204-1 through 204-M. For example, a first intermediate layer of the intermediate layers 204 may produce an output in the form of a first health indicator (e.g., a life expectancy), and a second intermediate layer of the intermediate layers 204, or the output layer 206, may produce an output in the form of a second health indicator (e.g., a life insurance premium), such that the second health indicator is determined based upon the first health indicator (and possibly some other input(s)).

In some embodiments, the neural network 200 may be a recurrent neural network, wherein decisions or outputs from at least one layer of the neural network 200 are fed back to at least one previous layer during training to provide an indication of significance (e.g., a "weight") of a particular input or intermediate layer output in determining a particular decision or calculation. For example, outputs of an intermediate layer 204 and/or output layer 206 may be utilized to weight personal activity metrics at the input layer 202. As a result of training, in some embodiments, insignificant inputs of inputs 202, and/or insignificant neurons of layers 204-1 through 204-M, may be bypassed in order to reduce processing demands in determining a health indicator of a person.

Figure 4:
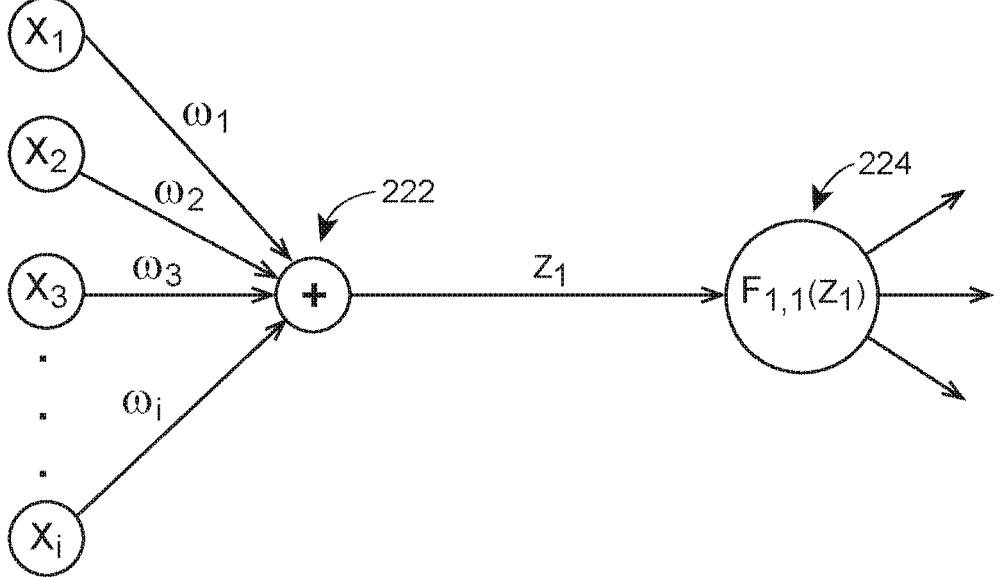
FIG. 4 depicts an example artificial neural network neuron that may be included in the artificial neural network of FIG. 3, in accordance with some embodiments.

FIG. 4 depicts an example neuron 220 that may correspond to a neuron of the neural network 200 of FIG. 3 (e.g., a neuron "1, 1" of the layer 204-1). One or more inputs $x_1$ through $x_i$ may be provided to 220. A particular input may be, for example, an input to the neural network 200 itself (e.g., a personal activity metric from an activity data set), or an output of a neuron of another layer of the neural network 200. Each input may be assigned a respective weight ($w_1$ through $w_i$), wherein the weight of each input may be determined during the training process. In some cases, an input may be determined to be insignificant to a decision or calculation of a neuron, and may accordingly be assigned a zero or near-zero weight.

The weighted inputs $x_1$ through $x_i$ may be provided to a summing node 222 of the neuron 220. The sum of the weighted inputs, $z_1$, may be provided as an input to a function 224, labeled in FIG. 4 as $F_{1,1}(z_1)$. The function 224 may represent any suitable linear or non-linear operation on $z_1$. As shown in FIG. 4, the output of function 224 may be provided to a number of neurons of the next layer, and/or may be provided as an output of neural network 200. For example, the output may indicate a location of a segment or segment portion, or may be a parameter that is calculated or determined as an interim step when determining such a location.

In other embodiments, and/or in other training scenarios, neuron 220 may be arranged differently than is shown in FIG. 4. For example, summing node 222 may be omitted, and function 224 may operate directly on one or more of the inputs $x_1$ through $x_i$. As another example, neuron 220 may not apply weights to any of the inputs $x_1$ through $x_i$.

Health Indicators and Their Utilization

The health indicators generated by the trained artificial neural network described above may generally be utilized to represent, in some direct or indirect manner, the health of a target person. A health indicator may be, for example, a life expectancy, a life insurance premium cost, or a health insurance premium cost for the target person. In some embodiments, a health indicator may be an overall "health score" representing an aggregate health (e.g., fitness) level of the target person. It should be understood that, in some cases, correlation may exist between different health indicators. A health score may, for example, be utilized at least in part to determine a life expectancy and/or life insurance premium for the target person. As another example, a target person's life expectancy may be a significant factor in determining a life insurance premium and/or other parameters of a life or health insurance policy.

In some embodiments, the health indicator may be utilized to "cross-sell" a life and/or health insurance policy to a target person already having some other insurance policy. The target person may have an existing automotive insurance policy, for example, in connection with which at least some sensor data is obtained from a mobile electronic device associated with the target person (e.g., as a part of a "good driving" rewards program). Based upon at least this sensor data, personal activity metrics may be derived, and an entity (e.g., an insurance provider) may utilize the artificial neural network to determine a health indicator and offer a life and/or health insurance policy to the automotive insurance customer, based at least in part upon the determined health indicator. Additionally or alternatively, the entity may utilize the artificial neural network to determine an updated health indicator of an existing life and/or health insurance customer, and update a life and/or health insurance premium, for example, based upon the determined health indicator.

Example Method For Determining a Health Indicator of a Person

Figure 5:
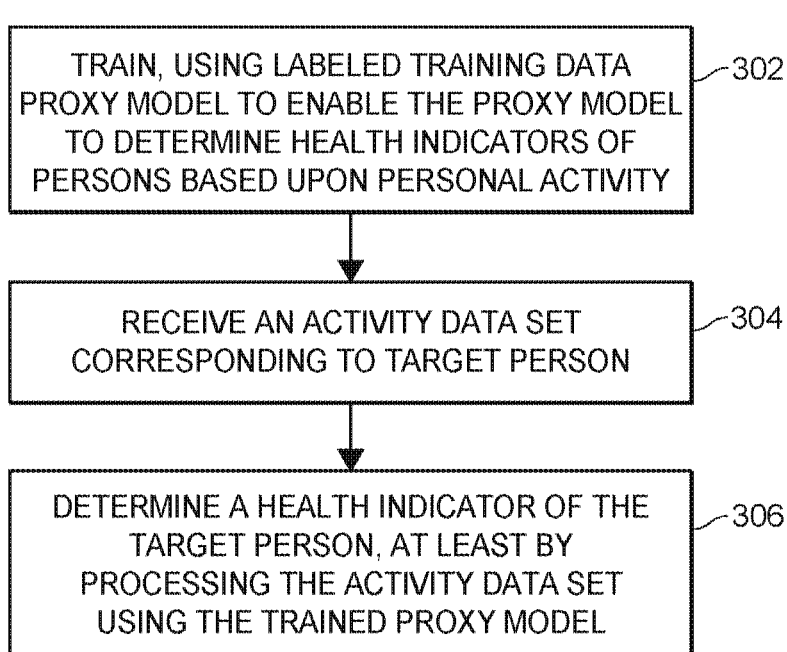
FIG. 5 depicts an example computer-implemented method for determining a health indicator of a target person using a proxy model as a proxy for a health assessment process, in accordance with some embodiments.

FIG. 5 illustrates an example computer-implemented method 300 for determining a health indicator of a target person using a proxy model (e.g., an artificial neural network) as a proxy for a health assessment process, in accordance with some embodiments. The method 300 may be performed, for example, by the server 140 of FIG. 2, or by both the mobile electronic device 112 and the server 140 of FIG. 2.

The method 300 may include training, using labeled training data, the proxy model to enable the proxy model to determine health indicators of persons based upon personal activity (block 302). The labeled training data may include, for example, a plurality of activity data training sets, each corresponding to a different one of a plurality of training persons. Each activity data training set may comprise a suite of personal activity metrics obtained or derived from (i.e., obtained from, and/or derived from sensor data obtained from) one or more mobile electronic devices of the respective training person. The training data may be "labeled" in that each activity data training set is labeled by one or more health indicators assigned to the respective training person by the health assessment process.

The health assessment process may be, in some embodiments, a partially or entirely manual process, and may include, for example, a physical examination and/or a process that relies upon medical history information associated with the respective training person (e.g., an underwriting process).

Training the proxy model may, in some embodiments, include comparing (i) a health indicator determined by the proxy model processing an activity data training set corresponding to a particular training person from among the training persons to (ii) a health indicator assigned to the particular training person by the health assessment process. In other words, a health indicator generated for a training person by the proxy model may be compared to the assigned or "known" health indicator for the same training person. This process may be performed iteratively, e.g., with various weights of the neural network being adjusted after each iteration, until the proxy model outputs, for some or all of the activity data training sets, a health indicator that matches (exactly, or within some acceptable margin of error) the known health indicator of the respective training person.

In some embodiments, the proxy model may be a recurrent neural network, and may include a plurality of hidden (or "intermediate") layers. As noted above, the training process may involve the adjustment of various weights of the neural network. For example, training the proxy model may include determining respective weights of one or more personal activity metrics provided as inputs to the proxy model. Additionally or alternatively, training the proxy model may include determining respective weights of one or more outputs generated by neurons of one or more of the plurality of hidden layers.

In some embodiments, one or more of the plurality of activity data training sets may be obtained via an application installed at respective mobile electronic devices of one or more respective training persons of the plurality of training persons. The application, when installed on a particular mobile electronic device, may be configured to obtain sensor data at a predetermined frequency of time, via activation of one or more sensors of the particular mobile electronic device.

The method 300 may further include receiving an activity data set corresponding to the target person (block 304). The activity data set corresponding to the target person may include a suite of personal activity metrics obtained or derived (i.e., obtained from, and/or derived from sensor data obtained from) from one or more mobile electronic devices of the target person.

In some embodiments, the activity data set corresponding to the target person may be obtained via an application installed at at least one device of the one or more mobile electronic devices of the target person. The application may be configured to obtain sensor data at a predetermined frequency of time, via activation of one or more sensors of the at least one device.

In some embodiments, training the proxy model includes identifying, from the one or more personal activity metrics, one or more significant metrics having a significant predictive effect upon the health indicator, and/or identifying one or more insignificant metrics not having a significant predictive effect upon the health indicator. In these embodiments, the application may be specifically configured to activate the one or more sensors of the at least one device to obtain sensor data associated with the one or more significant metrics, while not being configured to obtain and/or retain sensor data associated with the one or more insignificant metrics. Effectively, the application may be configured to activate one or more sensors of the at least one device in a manner to avoid unnecessary sensor activation.

The method 300 may further include determining a health indicator of the target person, at least by processing the activity data set using the trained proxy model (block 306). In some embodiments, the health indicator may be determined based upon other data (e.g., other health-related and/or financial data associated with the target person) in addition to the activity data set associated with the target person.

The method 300 may include additional, fewer, or alternate operations, in some embodiments.

Example Method For Health Assessment

Various embodiments can include an example computer-implemented method for health assessment. The method can comprise providing an artificial neural network trained with training data. The training data can include training metrics and health indicators corresponding to training persons. The training data can be based on data from mobile electronic devices associated with the training persons. The artificial neural network can be trained by at least identifying one or more first ones of the training metrics as having one or more predicted effects on one or more of the health indicators.

In many embodiments, the method further can include receiving activity data comprising personal activity metrics corresponding to a target person. The activity data can be based on data from one or more sensors associated with the target person and associated with one or more of the training metrics. The method also can include determining, by the artificial neural network, a health indicator of the target person based upon the activity data corresponding to the target person. Additionally, the method can include outputting the health indicator of the target person to an electronic device for communication of the health indicator to a user of the electronic device.

In some embodiments, the artificial neural network can be further trained by at least identifying one or more second ones of the training metrics as not having a predicted effect on one or more of the health indicators. The health indicators can be based on medical history information associated with the training persons. In a few embodiments, the artificial neural network can be trained with the training data by comparing a health indicator determined by the artificial neural network processing a portion of the training data corresponding to a particular training person of the training persons to a known health indicator assigned to the particular training person by a health assessment process. In a number of embodiments, the artificial neural network can include a recurrent neural network comprising hidden layers. The artificial neural network can be trained by determining respective weights of at least one of: (i) one or more activity metrics provided as one or more inputs to the artificial neural network, or (ii) one or more outputs generated by one or more of the hidden layers.

In several embodiments, the training data can be obtained from applications installed on the mobile electronic devices associated with the training persons. The applications can be configured to obtain sensor data from sensors of the mobile electronic devices at one or more predetermined frequencies of time.

In a number of embodiments, the activity data associated with the target person can be obtained from an application installed on at least one device associated with the target person, wherein the at least one device comprises the one or more sensors. The application can be configured to obtain sensor data from the one or more sensors at a predetermined frequency of time.

Example System For Health Assessment

Various embodiments can include an example computer system for health assessment. The computer system can comprise one or more processors and one or more memories storing computer-executable instructions. The computer-executable instructions, when executed by the one or more processors, can cause the computing system to perform one or more acts. In many embodiments, the one or more acts can include providing an artificial neural network trained with training data. The training data can comprise training metrics and health indicators corresponding to training persons. The training data can be based on data from mobile electronic devices associated with the training persons. Further, the artificial neural network can be trained by at least identifying one or more first ones of the training metrics as having one or more predicted effects on one or more of the health indicators.

In a number of embodiments, the one or more acts additionally can include receiving activity data comprising personal activity metrics corresponding to a target person. The activity data can be based on data from one or more sensors associated with the target person and associated with one or more of the training metrics. In some embodiments, the one or more acts also can include determining, by the artificial neural network, a health indicator of the target person based upon the activity data corresponding to the target person. In several embodiments, the one or more acts further can include outputting the health indicator of the target person to an electronic device for communication of the health indicator to a user of the electronic device.

In many embodiments, the artificial neural network can be further trained by at least identifying one or more second ones of the training metrics as not having a predicted effect on one or more of the health indicators. The health indicators can be based on medical history information associated with the training persons. In a number of embodiments, the artificial neural network can be trained with the training data by comparing a health indicator determined by the artificial neural network processing a portion of the training data corresponding to a particular training person of the training persons to a known health indicator assigned to the particular training person by a health assessment process.

In some embodiments, the artificial neural network can include a recurrent neural network comprising hidden layers. The artificial neural network can be trained by determining respective weights of at least one of: (i) one or more activity metrics provided as one or more inputs to the artificial neural network, or (ii) one or more outputs generated by one or more of the hidden layers. In a few embodiments, the training data can be obtained from applications installed on the mobile electronic devices associated with the training persons. The applications can be configured to obtain sensor data from sensors of the mobile electronic devices at one or more predetermined frequencies of time. In several embodiments, the activity data associated with the target person can be obtained from an application installed on at least one device associated with the target person. The at least one device can comprise the one or more sensors. The application can be configured to obtain sensor data from the one or more sensors at a predetermined frequency of time.

Example Medium For Health Assessment

Various embodiments can include an example non-transitory, computer-readable medium for health assessment. The non-transitory, computer-readable medium storing instructions, when executed by one or more processors, can cause the one or more processors to perform one or more acts. In many embodiments, the one or more acts can include providing an artificial neural network trained with training data. The training data can comprise training metrics and health indicators corresponding to training persons. The training data can be based on data from mobile electronic devices associated with the training persons. The artificial neural network can be trained by at least identifying one or more first ones of the training metrics as having one or more predicted effects on one or more of the health indicators.

In a number of embodiments, the one or more acts further can include receiving activity data comprising personal activity metrics corresponding to a target person. The activity data can be based on data from one or more sensors associated with the target person and associated with one or more of the training metrics. In several embodiments, the one or more acts further can include determining a health indicator of the target person based upon the activity data corresponding to the target person. In certain embodiments, the one or more acts further can include outputting the health indicator of the target person to an electronic device for communication of the health indicator to a user of the electronic device.

In a few embodiments, the artificial neural network can be further trained by at least identifying one or more second ones of the training metrics as not having a predicted effect on one or more of the health indicators. The health indicators can be based on medical history information associated with the training persons. In a number of embodiments, the artificial neural network is trained with the training data by comparing a health indicator determined by the artificial neural network processing a portion of the training data corresponding to a particular training person of the training persons to a known health indicator assigned to the particular training person by a health assessment process.

In some embodiments, the artificial neural network can comprise a recurrent neural network comprising hidden layers. The artificial neural network can be trained by determining respective weights of at least one of: (i) one or more activity metrics provided as one or more inputs to the artificial neural network, or (ii) one or more outputs generated by one or more of the hidden layers.

In many embodiments, the training data can be obtained from applications installed on the mobile electronic devices associated with the training persons. The applications can be configured to obtain sensor data from sensors of the mobile electronic devices at one or more predetermined frequencies of time. In a number of embodiments, the activity data associated with the target person can be obtained from an application installed on at least one device associated with the target person, wherein the at least one device comprises the one or more sensors. The application can be configured to obtain sensor data from the one or more sensors at a predetermined frequency of time.

ADDITIONAL CONSIDERATIONS

Although the following text sets forth a detailed description of numerous different embodiments, it should be understood that the legal scope of the invention may be defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that may be permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that may be temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it may be communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment, or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment.

The terms "insurer" and "insurance provider" may be used interchangeably herein to generally refer to a party or entity (e.g., a business or other organizational entity) that provides insurance products, e.g., by offering and issuing insurance policies. Typically, but not necessarily, an insurance provider may be an insurance company.

As used herein, the terms "comprises," "comprising," "may include," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also may include the plural unless it is obvious that it is meant otherwise.

This detailed description is to be construed as examples and does not describe every possible embodiment, as describing every possible embodiment would be impractical, if not impossible. One could implement numerous alternate embodiments, using either current technology or technology developed after the filing date of this application.

The patent claims at the end of this patent application are not intended to be constructed under 35 U.S.C. § 112(f), unless traditional means-plus-function language, such as "means for" or "step for" language, is explicitly recited in the claim(s). The systems and methods described herein are directed to an improvement in computer functionality, and improve the functioning of conventional computers.

What is claimed:

1. A computer-implemented method for health assessment, the method comprising:
   providing an artificial neural network trained with training data, wherein the training data comprises training metrics and health indicators corresponding to training persons, wherein:
      the training data is based on data from mobile electronic devices associated with the training persons; and
      the artificial neural network is trained by at least identifying one or more metrics beyond a predetermined weight threshold from the training data as having one or more predictive effects on one or more of the health indicators;
   receiving activity data comprising personal activity metrics corresponding to a target person, wherein:
      the activity data is based on data from one or more sensors associated with the target person and associated with one or more of the training metrics, wherein (1) the one or more sensors activate to obtain sensor data associated with the one or more metrics beyond the predetermined weight threshold and (2) the one or more sensors deactivate to not obtain sensor data not associated with the one or more metrics beyond the predetermined weight threshold; and the personal activity metrics comprise an average walking speed for the target person over a predetermined period of time;

determining, by the artificial neural network, a first health indicator and a second health indicator of the health indicators of the target person based upon the activity data corresponding to the target person, wherein:

the artificial neural network comprises a first intermediate layer to output the first health indicator, and a second intermediate layer to output the second health indicator;

the second health indicator is based on at least the first health indicator;

the first health indicator comprises at least one of a health score for the target person or a life expectancy of the target person; and the second health indicator comprises at least one of a life insurance premium for the target person or a health insurance premium cost for the target person; and outputting the first health indicator and the second health indicator of the target person to an electronic device for communication of the first health indicator and the second health indicator to a user of the electronic device.

2. The computer-implemented method of claim 1, wherein the artificial neural network is further trained by at least identifying one or more metrics not associated with the one or more metrics beyond the predetermined weight threshold from the training metrics as not having the one or more predictive effects on one or more of the health indicators.

3. The computer-implemented method of claim 1, wherein the health indicators are based on medical history information associated with the training persons.

4. The computer-implemented method of claim 1, wherein the artificial neural network is further trained with the training data by comparing a health indicator determined by the artificial neural network processing a portion of the training data corresponding to a particular training person of the training persons to a known health indicator assigned to the particular training person by a health assessment process.

5. The computer-implemented method of claim 1, wherein the artificial neural network comprises a recurrent neural network comprising hidden layers, and wherein the artificial neural network is trained by determining respective weights of at least one of: (i) one or more activity metrics provided as one or more inputs to the artificial neural network, or (ii) one or more outputs generated by one or more of the hidden layers.

6. The computer-implemented method of claim 1, wherein:

the training data is obtained from applications installed on the mobile electronic devices associated with the training persons; and the applications are configured to obtain the sensor data associated with the one or more metrics beyond the predetermined weight threshold from sensors of the mobile electronic devices at one or more predetermined frequencies of time.

7. The computer-implemented method of claim 1, wherein:

the activity data associated with the target person is obtained from an application installed on at least one device associated with the target person, wherein the at least one device comprises the one or more sensors; and the application is configured to obtain the sensor data associated with the one or more metrics beyond the predetermined weight threshold from the one or more sensors at a predetermined frequency of time.

8. A computer system for health assessment, the computer system comprising:

one or more processors; and one or more memories storing computer-executable instructions that, when executed by the one or more processors, cause the computing system to:

provide an artificial neural network trained with training data, wherein the training data comprises training metrics and health indicators corresponding to training persons, wherein:

the training data is based on data from mobile electronic devices associated with the training persons; and the artificial neural network is trained by at least identifying one or more metrics beyond a predetermined weight threshold from the training data as having one or more predictive effects on one or more of the health indicators;

receive activity data comprising personal activity metrics corresponding to a target person, wherein:

the activity data is based on data from one or more sensors associated with the target person and associated with one or more of the training metrics, wherein (1) the one or more sensors activate to obtain sensor data associated with the one or more metrics beyond the predetermined weight threshold and (2) the one or more sensors deactivate to not obtain sensor data not associated with the one or more metrics beyond the predetermined weight threshold; and the personal activity metrics comprise an average walking speed for the target person over a predetermined period of time;

determine, by the artificial neural network, a first health indicator and a second health indicator of the target person based upon the activity data corresponding to the target person, wherein:

the artificial neural network comprises a first intermediate layer to output the first health indicator, and a second intermediate layer to output the second health indicator;

the second health indicator is based on at least the first health indicator;

the first health indicator comprises at least one of a health score for the target person or a life expectancy of the target person; and the second health indicator comprises at least one of a life insurance premium for the target person or a health insurance premium cost for the target person; and output the first health indicator and the second health indicator of the target person to an electronic device for communication of the first health indicator and the second health indicator to a user of the electronic device.

9. The computer system of claim 8, wherein the artificial neural network is further trained by at least identifying one or more metrics not associated with the one or more metrics beyond the predetermined weight threshold from the training metrics as not having the one or more predictive effects on one or more of the health indicators.

10. The computer system of claim 8, wherein the health indicators are based on medical history information associated with the training persons.

11. The computer system of claim 8, wherein the artificial neural network is further trained with the training data by comparing a health indicator determined by the artificial neural network processing a portion of the training data corresponding to a particular training person of the training persons to a known health indicator assigned to the particular training person by a health assessment process.

12. The computer system of claim 8, wherein the artificial neural network comprises a recurrent neural network comprising hidden layers, and wherein the artificial neural network is trained by determining respective weights of at least one of: (i) one or more activity metrics provided as one or more inputs to the artificial neural network, or (ii) one or more outputs generated by one or more of the hidden layers.

13. The computer system of claim 8, wherein:

the training data is obtained from applications installed on the mobile electronic devices associated with the training persons; and the applications are configured to obtain the sensor data associated with the one or more metrics beyond the predetermined weight threshold from sensors of the mobile electronic devices at one or more predetermined frequencies of time.

14. The computer system of claim 8, wherein:

the activity data associated with the target person is obtained from an application installed on at least one device associated with the target person, wherein the at least one device comprises the one or more sensors; and the application is configured to obtain the sensor data associated with the one or more metrics beyond the predetermined weight threshold from the one or more sensors at a predetermined frequency of time.

15. A non-transitory, computer-readable medium for health assessment, the non-transitory, computer-readable medium storing instructions that, when executed by one or more processors, cause the one or more processors to:

provide an artificial neural network trained with training data, wherein the training data comprises training metrics and health indicators corresponding to training persons, wherein:

the training data is based on data from mobile electronic devices associated with the training persons; and the artificial neural network is trained by at least identifying one or more metrics beyond a predetermined weight threshold from the training data as having one or more predictive effects on one or more of the health indicators;

receive activity data comprising personal activity metrics corresponding to a target person, wherein:

the activity data is based on data from one or more sensors associated with the target person and associated with one or more of the training metrics, wherein (1) the one or more sensors activate to obtain sensor data associated with the one or more metrics beyond the predetermined weight threshold and (2) the one or more sensors deactivate to not obtain sensor data not associated with the one or more metrics beyond the predetermined weight threshold; and the personal activity metrics comprise an average walking speed for the target person over a predetermined period of time;

determine, by the artificial neural network, a first health indicator and a second health indicator of the health indicators of the target person based upon the activity data corresponding to the target person, wherein:

the artificial neural network comprises a first intermediate layer to output the first health indicator, and a second intermediate layer to output the second health indicator;

the second health indicator is based on at least the first health indicator;

the first health indicator comprises at least one of a health score for the target person or a life expectancy of the target person; and the second health indicator comprises at least one of a life insurance premium for the target person or a health insurance premium cost for the target person; and output the first health indicator and the second health indicator of the target person to an electronic device for communication of the first health indicator and the second health indicator to a user of the electronic device.

16. The non-transitory, computer-readable medium of claim 15, wherein one or more of:

the artificial neural network is further trained by at least identifying one or more metrics not associated with the one or more metrics beyond the predetermined weight threshold from the training metrics as not having the one or more predictive effects on one or more of the health indicators; or the health indicators are based on medical history information associated with the training persons.

17. The non-transitory, computer-readable medium of claim 15, wherein the artificial neural network is further trained with the training data by comparing a health indicator determined by the artificial neural network processing a portion of the training data corresponding to a particular training person of the training persons to a known health indicator assigned to the particular training person by a health assessment process.

18. The non-transitory, computer-readable medium of claim 15, wherein the artificial neural network comprises a recurrent neural network comprising hidden layers, and wherein the artificial neural network is trained by determining respective weights of at least one of: (i) one or more activity metrics provided as one or more inputs to the artificial neural network, or (ii) one or more outputs generated by one or more of the hidden layers.

19. The non-transitory, computer-readable medium of claim 15, wherein:

the training data is obtained from applications installed on the mobile electronic devices associated with the training persons; and the applications are configured to obtain the sensor data associated with the one or more metrics beyond the predetermined weight threshold from sensors of the mobile electronic devices at one or more predetermined frequencies of time.

20. The non-transitory, computer-readable medium of claim 15, wherein:

the activity data associated with the target person is obtained from an application installed on at least one device associated with the target person, wherein the at least one device comprises the one or more sensors; and the application is configured to obtain the sensor data associated with the one or more metrics beyond the predetermined weight threshold from the one or more sensors at a predetermined frequency of time.

* * * * *